(12) United States Patent
Liu et al.

(10) Patent No.: US 12,080,538 B2
(45) Date of Patent: Sep. 3, 2024

(54) WATER-CONTAINING SIMULATED LUNAR SOIL PREPARATION AND WATER CONTENT MEASUREMENT SYSTEM AND METHOD

(71) Applicant: Institute of Geology and Geophysics, CAS, Beijing (CN)

(72) Inventors: Ziheng Liu, Beijing (CN); Jiannan Li, Beijing (CN); Fei Su, Beijing (CN); Huaiyu He, Beijing (CN)

(73) Assignee: Institute of Geology and Geophysics, CAS, Beijing (CN)

( * ) Notice: Subject to any disclaimer, the term of this patent is extended or adjusted under 35 U.S.C. 154(b) by 0 days.

(21) Appl. No.: 18/514,444

(22) Filed: Nov. 20, 2023

(65) Prior Publication Data
US 2024/0242952 A1    Jul. 18, 2024

(30) Foreign Application Priority Data
Jan. 13, 2023    (CN) .......................... 202310072309.0

(51) Int. Cl.
*H01J 49/04* (2006.01)
*G01N 33/18* (2006.01)
(Continued)

(52) U.S. Cl.
CPC .......... *H01J 49/0459* (2013.01); *G01N 33/18* (2013.01); *H01J 49/0468* (2013.01);
(Continued)

(58) Field of Classification Search
CPC ...... G01N 33/18; H01J 49/04; H01J 49/0459; H01J 49/0468; H01J 49/0495; H01J 49/24; H01J 49/4205
(Continued)

(56) References Cited

FOREIGN PATENT DOCUMENTS

| CN | 111975937 | 11/2020 |
|---|---|---|
| CN | 113984603 | 1/2022 |

(Continued)

OTHER PUBLICATIONS

Notice of opinion for the first review for Chinese Patent Application No. 202310072309.0, issued Jun. 14, 2023, 15 pages.
(Continued)

*Primary Examiner* — Maureen Wallenhorst
(74) *Attorney, Agent, or Firm* — DLA PIPER LLP (US)

(57) ABSTRACT

A water-containing simulated lunar soil preparation and water content measurement system and method is provided. The system includes a water-containing simulated lunar soil preparation unit, a low-pressure environment simulation unit, and a water content analysis unit. The water-containing simulated lunar soil preparation unit includes a preparation pipeline, a low-temperature lunar soil cold trap, and a low-temperature water ice cold trap. Both ends of the preparation pipeline are connected with the low-temperature lunar soil cold trap and the low-temperature water ice cold trap through a first opening and closing valve and a second opening and closing valve, respectively. The low-pressure environment simulation unit includes a low-pressure pipeline provided with a vacuum pump. Both ends of the low-pressure pipeline are connected with the preparation pipeline and the water content analysis unit through a first pneumatic valve and a second pneumatic valve, respectively.

12 Claims, 1 Drawing Sheet

(51) Int. Cl.
  *H01J 49/24* (2006.01)
  *H01J 49/42* (2006.01)
(52) U.S. Cl.
  CPC .......... *H01J 49/0495* (2013.01); *H01J 49/24* (2013.01); *H01J 49/4205* (2013.01)
(58) Field of Classification Search
  USPC ........................ 436/25, 39, 43, 55, 173, 181
  See application file for complete search history.

(56) References Cited

FOREIGN PATENT DOCUMENTS

| | | | |
|---|---|---|---|
| CN | 115524205 A | * | 12/2022 |
| CN | 115901399 A | * | 1/2023 |
| CN | 113432931 | | 2/2023 |
| CN | 115950707 | | 8/2023 |
| WO | 2019/165907 A1 | * | 9/2019 |

OTHER PUBLICATIONS

Notification to Grant Patent Right for Invention for Chinese Patent Application No. 202310072309.0, issued Jul. 28, 2023, 6 pages.

\* cited by examiner

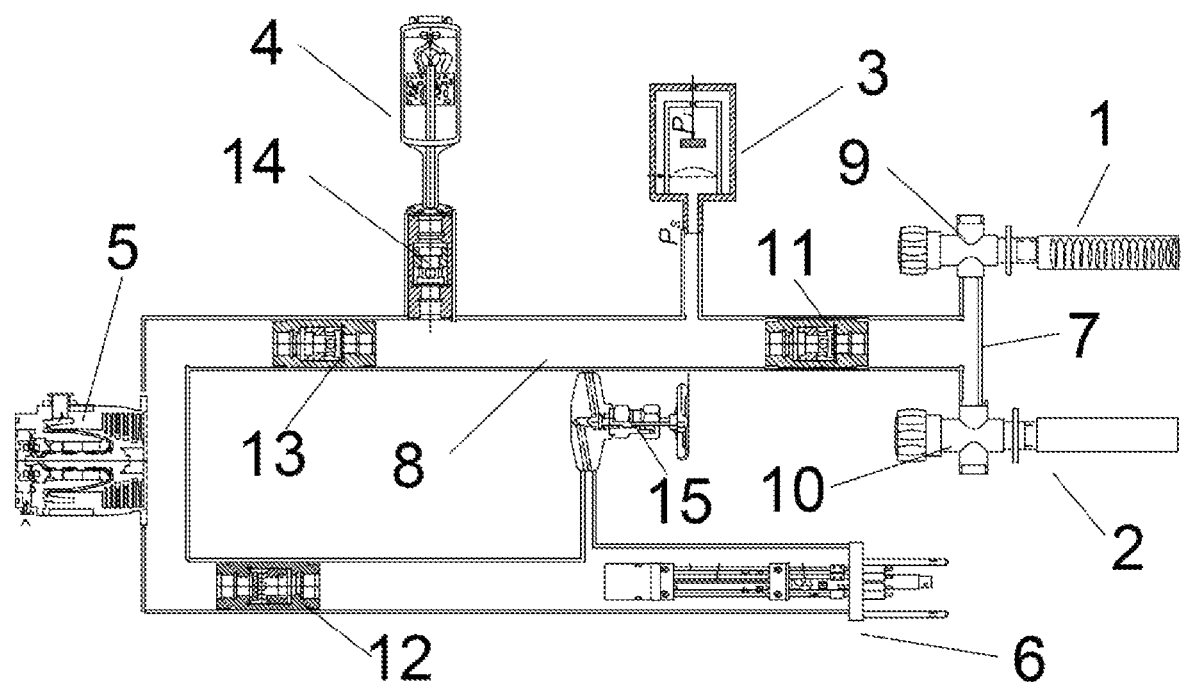

WATER-CONTAINING SIMULATED LUNAR SOIL PREPARATION AND WATER CONTENT MEASUREMENT SYSTEM AND METHOD

CROSS-REFERENCE TO RELATED APPLICATION

This patent application claims the benefit and priority of Chinese Patent Application No. 202310072309.0 filed with the China National Intellectual Property Administration on Jan. 13, 2023, the disclosure of which is incorporated by reference herein in its entirety as part of the present application.

TECHNICAL FIELD

The present disclosure relates to the technical field of soil detection, and in particular, to a water-containing simulated lunar soil preparation and water content measurement system and a method.

BACKGROUND

There may be a large amount of water ice in a permanent shadow area of a lunar polar region. The water ice is of great significance for future research bases. However, there is a lack of reliable methods for detecting the water ice at present. In order to verify the effectiveness of a water ice detection scheme, it is necessary to prepare corresponding water-containing simulated lunar soil, and moreover it is necessary to determine the water content of the water-containing simulated lunar soil. At present, a method of adding water and stirring is usually used for analyzing the water-containing simulated lunar soil and a method of weighing by a heated balance is used for determining the water content. However, by the traditional methods of preparation and measurement mentioned above, there is a significant difference in the occurrence state of water between the prepared water-containing simulated lunar soil and the actual lunar soil on the lunar surface, and moreover, the method of weighing by the balance will cause interference from other volatile components in the measurement results. Because the permanent shadow area of the lunar soil is in a low-temperature and low-pressure state, the water-containing simulated lunar soil contains more water vapor than liquid water, and the water vapor in the simulated lunar soil is easy to volatilize during sample transfer and measurement, resulting in a significant change in the water content before and after the measurement.

The invention patent with the patent number CN202110582255.3 discloses a simulation experimental device for extracting water vapor from water ice-containing lunar soil, which includes a main body cavity, a control unit, a liquid nitrogen conveying unit, and a vacuum equipment unit. The experimental steps using the simulation experimental device include: starting the vacuum equipment unit and the liquid nitrogen conveying unit: extracting the water vapor from the water ice by a local heating method when a vacuum parameter and a temperature parameter of the main body cavity reach the set threshold values: transmitting the extracted water vapor to a water vapor analysis instrument for further water vapor analysis. The advantage of the above invention is that the local water vapor extraction process of lunar water ice in a low-temperature and vacuum lunar environment can be simulated. However, the above patent can only be used for the measurement of the water content but cannot be used for preparing water-containing lunar soil. Additional water-containing lunar soil needs to be provided. The water content in the water-containing lunar soil is inevitably lost during the transfer process to the experimental device for extracting the water vapor. Moreover, the details of preparing the water-containing lunar soil are not disclosed in the above patent, so the restorability of the water-containing lunar soil cannot be known.

SUMMARY

An objective of the present disclosure is to provide a water-containing simulated lunar soil preparation and water content measurement system and method to solve the above technical problems, which combines both a preparation of the water-containing simulated lunar soil and a measurement of the water content. During the preparation, a low-pressure and low-temperature environment of the lunar soil can be simulated, so as to restore the authenticity of the water-containing lunar soil to the greatest extent. Meanwhile, the water-containing simulated lunar soil is in this system from the preparation process to the measurement process, which ensures that there is no problem of water vapor loss between the processes, thereby improving the accuracy of the measurement.

To achieve the above objective, the present disclosure provides the following solution: embodiments of the present disclosure relate to a water-containing simulated lunar soil preparation and water content measurement system, which includes a water-containing simulated lunar soil preparation unit, a low-pressure environment simulation unit, and a water content analysis unit. The water-containing simulated lunar soil preparation unit includes a preparation pipeline, a low-temperature lunar soil cold trap filled with simulated lunar soil, and a low-temperature water ice cold trap filled with solid ice. An end of the preparation pipeline is connected with the low-temperature lunar soil cold trap through a first switch valve, and an other end of the preparation pipeline is connected with the low-temperature water ice cold trap through a second switch valve. The low-pressure environment simulation unit includes a low-pressure pipeline provided with a vacuum pump. An end of the low-pressure pipeline communicates with the preparation pipeline through a first pneumatic valve, and an other end of the low-pressure pipeline is connected with the water content analysis unit through a second pneumatic valve.

Preferably, the water content analysis unit includes a quadrupole mass spectrometer.

Preferably, the quadrupole mass spectrometer communicates with the second pneumatic valve through a flow regulating valve.

Preferably, a third pneumatic valve is provided between the first pneumatic valve and the second pneumatic valve. A diaphragm gauge in communication with the low-pressure pipeline is provided between the third pneumatic valve and the first pneumatic valve.

Preferably, an ion gauge is provided between the third pneumatic valve and the first pneumatic valve. The ion gauge is connected with the low-pressure pipeline through a fourth pneumatic valve.

Preferably, both the first switch valve and the second switch valve are manual angle valves. Preferably, the vacuum pump is a molecular pump.

The present disclosure further discloses a water-containing simulated lunar soil preparation and water content measurement method using the water-containing simulated lunar soil preparation and water content measurement system mentioned above, which includes the following steps:

S1: a preparation of the water-containing simulated lunar soil: opening the first switch valve, the second switch valve, the first pneumatic valve, and the second pneumatic valve, starting the vacuum pump to vacuum, closing the first pneumatic valve and the second pneumatic valve after pressures in the low-pressure pipeline and the preparation pipeline are reduced to preset values, regulating temperatures of the low-temperature lunar soil cold trap and the low-temperature water ice cold trap to enable the solid ice in the low-temperature water ice cold trap to melt and release water vapor to prepare the water-containing simulated lunar soil, and closing the second switch valve after the water-containing simulated lunar soil is prepared successfully; and S2: a measurement of the water content of the water-containing simulated lunar soil: opening the first pneumatic valve and the second pneumatic valve, heating the low-temperature lunar soil cold trap, and measuring the water content by the water content analysis unit.

Preferably, in S2, closing the second pneumatic valve and the third pneumatic valve before opening the first pneumatic valve, then measuring the water content by the diaphragm gauge, opening the flow regulating valve if the water content is low; and measuring the water content in the water-containing simulated lunar soil using the quadrupole mass spectrometer.

Preferably, in S1, opening the fourth pneumatic valve to measure pressures in the low-pressure pipeline and the preparation pipeline after the vacuum pump is started, and closing the first pneumatic valve and the second pneumatic valve after the pressures in the low-pressure pipeline and the preparation pipeline are reduced to 0.00001 Pa.

Compared with the prior art, the embodiments of the present disclosure achieve the following technical effects:

1. In the present disclosure, the system can be vacuumized through the vacuum pump, so as to simulate the low-pressure environment in a permanent shadow area of a lunar polar region. And the temperatures of the low-temperature lunar soil cold trap and the low-temperature water ice cold trap are regulated, which can simulate the low-temperature environment in the permanent shadow area of the lunar polar region. The water-containing simulated soil prepared in the low-pressure and low-temperature environment can restore the water content of the real lunar soil in the permanent shadow area of the lunar polar region to the greatest extent. Both the preparation and the measurement are conducted in the same system, the water vapor will not leak out, which can ensure that the water vapor before and after the measurement will not lose, thereby improving the accuracy of the measurement.

2. In the present disclosure, the diaphragm gauge is provided between the first pneumatic valve and the second pneumatic valve. After the water-containing simulated lunar soil is prepared, the water content of the water-containing simulated lunar soil can be measured in advance by the diaphragm gauge. If there is much water vapor, it indicates that a water pressure is high, the flow is reduced through the flow regulating valve, then the second pneumatic valve is opened for the measurement, which can protect the quadrupole mass spectrometer from being damaged due to excessive water pressure.

BRIEF DESCRIPTION OF THE DRAWINGS

To describe the technical solutions in the embodiments of the present disclosure or in the prior art more clearly, the following briefly describes the drawings required for describing the embodiments. Apparently, the drawings in the following description show merely some embodiments of the present disclosure, and those of ordinary skill in the art may still derive other drawings from these drawings without creative efforts.

FIG. 1 is a water-containing simulated lunar soil preparation and water content measurement system.

Reference signs in the drawings: 1, low-temperature lunar cold trap; 2, low-temperature water ice cold trap; 3, diaphragm gauge; 4, ion gauge; 5, vacuum pump; 6, quadrupole mass spectrometer; 7, preparation pipeline; 8, low-temperature pipeline; 9, first switch valve; 10, second switch valve; 11, first pneumatic valve; 12, second pneumatic valve; 13, third pneumatic valve; 14, fourth pneumatic valve; and 15, flow regulating valve.

DETAILED DESCRIPTION OF THE EMBODIMENTS

Technical solutions in the embodiments of the present disclosure will be clearly and completely described below with reference to the drawings in the embodiments of the present disclosure. Apparently, the described embodiments are merely part rather than all of the embodiments of the present disclosure. On the basis of the embodiments of the present disclosure, all other embodiments obtained by those of ordinary skill in the art without creative work fall within the scope of protection of the present disclosure.

Embodiment 1

This embodiment provides a water-containing simulated lunar soil preparation and water content measurement system, as shown in FIG. 1, the water-containing simulated lunar soil preparation and water content measurement system includes a water-containing simulated lunar soil preparation unit, a low-pressure environment simulation unit, and a water content analysis unit. The water-containing simulated lunar soil preparation unit includes a low-temperature lunar soil cold trap 1, a low-temperature water ice cold trap 2, and a preparation pipeline 7. The low-temperature lunar soil cold trap 1 is filled with simulated lunar soil. The low-temperature water ice cold trap 2 is filled with solid ice. An end of the preparation pipeline 7 communicates with the low-temperature lunar soil cold trap 1 through a first switch valve 9, and the other end of the preparation pipeline 7 communicates with the low-temperature water ice cold trap 2 through a second switch valve 10. The low-pressure environment simulation unit includes a low-pressure pipeline 8 provided with a vacuum pump 5. An end of the low-pressure pipeline 8 communicates with the preparation pipeline 7 through a first pneumatic valve 11, and the other end of the low-pressure pipeline 8 is connected with the water content analysis unit through a second pneumatic valve 12.

When the water-containing simulated lunar soil is prepared, the first pneumatic valve 11, the second pneumatic valve 12, the first switch valve 9, and the second switch valve 10 need to be opened first, and then the vacuum pump 5 is started to vacuum. The vacuum pump 5, the pneumatic valve 11, and the second pneumatic valve 12 are closed when reaching the same low pressure as a permanent shadow area of a lunar polar region. The temperatures of the low-temperature water ice cold trap 2 and the low-temperature lunar soil cold trap 1 are regulated to be the same as that of a low-temperature environment of the permanent shadow area of the lunar polar region, so that the solid ice in the low-temperature water ice cold trap 2 heats up and releases water vapor. The water vapor enters the low-temperature lunar soil cold trap 1 through the preparation pipeline 7. When the water content of the simulated lunar soil in the low-temperature lunar soil cold trap 1 reaches the same level as the water vapor content of the lunar soil in the permanent shadow area of the lunar polar region, the second switch valve 10 is closed to complete the preparation of the water-containing simulated lunar soil. Since the low-temperature lunar soil cold trap 1, the low-temperature water ice cold trap 2, and the preparation pipeline 7 are located in the same low-pressure and low-temperature environment as the permanent shadow area of the lunar polar region, the water content of the prepared water-containing simulated lunar soil can restore that of the real lunar soil to the greatest extent. Preferably, the pressure of the low-pressure environment of the entire system is to be kept at 0.1 Pa to 0.00001 Pa, preferably 0.00001 Pa. When the water-containing lunar soil is prepared, the temperatures of the low-temperature lunar soil cold trap 1 and the low-temperature water ice cold trap 2 are to be 80 k to 350 k. The water content can reach 0.5% to 10% to meet the preparation standards.

When the water content of the water-containing simulated lunar soil is measured, the first pneumatic valve 11 and the second pneumatic valve 12 are opened, the low-temperature lunar soil cold trap 1 is heated, and the water-containing simulated soil can be measured by the water content analysis unit. Since the water-containing simulated lunar soil is in the closed system from the preparation to the measurement, the water vapor in the water-containing lunar soil will not evaporate to the outside world, thereby ensuring the accuracy of the measurement. In addition, the measurement of which measurement equipment is the most accurate can be obtained by replacing different forms of measurement equipment to repeat the above preparation and measurement. In this embodiment, measurement equipment with relatively accurate measurement is provided. As shown in FIG. 1, the water content analysis unit includes a quadrupole mass spectrometer 6. The quadrupole mass spectrometer 6 has the mass number of 1 to 25 amu, the resolution of less than 1 amu, and a detection line of 1 ppm.

Further, in this embodiment, as shown in FIG. 1, the quadrupole mass spectrometer 6 communicates with the second pneumatic valve 12 through a flow regulating valve 15.

In this embodiment, as shown in FIG. 1, a third pneumatic valve 13 is provided between the first pneumatic valve 11 and the second pneumatic valve 12. A diaphragm gauge 3 is provided between the third pneumatic valve 13 and the first pneumatic valve 11, and the diaphragm gauge 3 communicates with the low-pressure pipeline 8. After the water-containing simulated lunar soil is prepared, the first pneumatic valve 11 is opened first and, at this moment, both the second pneumatic valve 12 and the third pneumatic valve 13 are kept closed, and then the water content of the water-containing simulated lunar soil is measured by the diaphragm gauge 3 in advance. If the pressure of the water vapor is high, the second pneumatic valve 12 is not opened for the measurement first to protect the quadrupole mass spectrometer 6 from being damaged due to high pressure. Then, the flow at an air inlet is reduced first by the flow regulating valve 15, and then the second pneumatic valve 12 is opened for the measurement.

Further, in this embodiment, as shown in FIG. 1, an ion gauge 4 is provided between the third pneumatic valve 13 and the first pneumatic valve 11. The ion gauge 4 is connected with the low-pressure pipeline 8 through a fourth pneumatic valve 14. When the vacuum pump 5 is used for vacuuming, the degree of low pressure in the low-pressure pipeline 8 is detected by the ion gauge 4, and the fourth pneumatic valve 14 is closed after the standards are met.

In this embodiment, as shown in FIG. 1, both the first switch valve 9 and the second switch valve 10 are manual angle valves.

In this embodiment, as shown in FIG. 1, the vacuum pump 5 is a molecular pump.

Embodiment 2

This embodiment provides a water-containing simulated lunar soil preparation and water content measurement method using the water-containing simulated lunar soil preparation and water content measurement system in Embodiment 1, which includes the following steps:

Step 1, preparation of a water-containing simulated lunar soil: the first switch valve 9, the second switch valve 10, the first pneumatic valve 11, and the second pneumatic valve 12 are opened, the vacuum pump 5 is started to vacuum. The first pneumatic valve 11 and the second pneumatic valve 12 are closed after the pressures in the low-pressure pipeline 8 and the preparation pipeline 7 are reduced to preset values. The temperatures of the low-temperature lunar soil cold trap 1 and the low-temperature water ice cold trap 2 are regulated to enable the solid ice in the low-temperature water ice cold trap 2 to melt and release water vapor, and the simulated lunar soil in the low-temperature lunar soil cold trap 1 absorbs the water vapor to prepare the water-containing simulated lunar soil. And the second switch valve 10 is closed after the water-containing simulated lunar soil is prepared successfully with the water content reaches 0.5% to 10%.

Step 2, measurement of the water content of the water-containing simulated lunar soil: the first pneumatic valve 11 and the second pneumatic valve 12 are opened, the low-temperature lunar soil cold trap 1 is heated, and the water content is measured by the water content analysis unit.

In this embodiment, as shown in FIG. 1, in Step 2, the second pneumatic valve 12 and the third pneumatic valve 13 are closed before the first pneumatic valve 11 is opened, then the water content is measured by the diaphragm gauge 3. If there is much water vapor, it indicates that the pressure of the water vapor is high, and the flow regulating valve 15 is opened to regulate the flow to protect the quadrupole mass spectrometer 6.

Further, in this embodiment, as shown in FIG. 1, in Step 1, the fourth pneumatic valve 14 is opened to measure the pressures in the low-pressure pipeline 8 and the preparation pipeline 7 after the vacuum pump 5 is started, and the first pneumatic valve 11 and the second pneumatic valve 12 are closed after the pressures in the low-pressure pipeline 8 and the preparation pipeline 7 are reduced to 0.00001 Pa.

In this embodiment, as shown in FIG. 1, before Step 1, the method further includes Step 0, the low-temperature water ice cold trap 2 is placed in liquid nitrogen, then liquid water is injected slowly, and the low-temperature water ice cold trap 2 is connected to the second switch valve 10 through a vacuum flange after the liquid water freezes into ice completely, so as to form the low-temperature water ice cold trap 2 filled with solid ice. After quantitative simulated lunar soil is placed into the low-temperature lunar soil cold trap 1, the low-temperature lunar soil cold trap 1 is connected to the first switch valve 9 also through a vacuum flange, then Step 1 may be performed.

Specific examples are applied in the present disclosure to illustrate the principle and implementation mode of the present disclosure. The description of the above embodiments is merely used to help understand the method and its core principle of the present disclosure. Meanwhile, for those of ordinary skill in the art, there will be changes in the specific implementation mode and application scope according to the principle of the present disclosure. In conclusion, the content of the present specification shall not be construed as a limitation to the present disclosure.

What is claimed is:

1. A water-containing simulated lunar soil preparation and water content measurement system, comprising:
    a water-containing simulated lunar soil preparation unit,
    a low-pressure environment simulation unit, and
    a water content analysis unit, wherein the water-containing simulated lunar soil preparation unit comprises:
        a preparation pipeline,
        a low-temperature lunar soil cold trap filled with simulated lunar soil, and
        a low-temperature water ice cold trap filled with solid ice;
        wherein an end of the preparation pipeline is connected with the low-temperature lunar soil cold trap through a first switch valve, and an other end of the preparation pipeline is connected with the low-temperature water ice cold trap through a second switch valve;
        wherein the low-pressure environment simulation unit comprises a low-pressure pipeline provided with a vacuum pump; and
        wherein an end of the low-pressure pipeline communicates with the preparation pipeline through a first pneumatic valve, and an other end of the low-pressure pipeline is connected with the water content analysis unit through a second pneumatic valve;
        wherein when a water content of water-containing simulated lunar soil is measured, the first pneumatic valve and the second pneumatic valve are opened and the low-temperature lunar soil cold trap is heated;
        wherein the water content is measured by the water content analysis unit;
        wherein the water content analysis unit comprises a quadrupole mass spectrometer; and
        wherein pressures of the low-pressure environment simulation unit and the low-pressure pipeline are to be kept at 0.1 Pa to 0.00001 Pa, and temperatures of the low-temperature lunar soil cold trap and the low-temperature water ice cold trap are to be 80 k to 350 k.

2. The water-containing simulated lunar soil preparation and water content measurement system according to claim 1, wherein the quadrupole mass spectrometer communicates with the second pneumatic valve through a flow regulating valve.

3. The water-containing simulated lunar soil preparation and water content measurement system according to claim 2, wherein a third pneumatic valve is provided between the first pneumatic valve and the second pneumatic valve; and a diaphragm gauge in communication with the low-pressure pipeline is provided between the third pneumatic valve and the first pneumatic valve.

4. The water-containing simulated lunar soil preparation and water content measurement system according to claim 3, wherein an ion gauge is provided between the third pneumatic valve and the first pneumatic valve; and the ion gauge is connected with the low-pressure pipeline through a fourth pneumatic valve.

5. The water-containing simulated lunar soil preparation and water content measurement system according to claim 4, wherein both the first switch valve and the second switch valve are manual angle valves.

6. The water-containing simulated lunar soil preparation and water content measurement system according to claim 4, wherein the vacuum pump is a molecular pump.

7. A water-containing simulated lunar soil preparation and water content measurement method using a water-containing simulated lunar soil preparation and water content measurement system, the system comprising:
    a water-containing simulated lunar soil preparation unit,
    a low-pressure environment simulation unit, and
    a water content analysis unit,
    wherein the water-containing simulated lunar soil preparation unit comprises:
        a preparation pipeline,
        a low-temperature lunar soil cold trap filled with simulated lunar soil, and
        a low-temperature water ice cold trap filled with solid ice;
        wherein an end of the preparation pipeline is connected with the low-temperature lunar soil cold trap through a first switch valve, and an other end of the preparation pipeline is connected with the low-temperature water ice cold trap through a second switch valve;
        wherein the low-pressure environment simulation unit comprises a low-pressure pipeline provided with a vacuum pump; and
        wherein an end of the low-pressure pipeline communicates with the preparation pipeline through a first pneumatic valve, and an other end of the low-pressure pipeline is connected with the water content analysis unit through a second pneumatic valve;
        wherein when a water content of water-containing simulated lunar soil is measured, the first pneumatic valve and the second pneumatic valve are opened and the low-temperature lunar soil cold trap is heated;
        wherein the water content is measured by the water content analysis unit; and
        wherein the water content analysis unit comprises a quadrupole mass spectrometer;
        wherein the quadrupole mass spectrometer communicates with the second pneumatic valve through a flow regulating valve;
        wherein a third pneumatic valve is provided between the first pneumatic valve and the second pneumatic valve; and
        wherein a diaphragm gauge in communication with the low-pressure pipeline is provided between the third pneumatic valve and the first pneumatic valve;
        wherein an ion gauge is provided between the third pneumatic valve and the first pneumatic valve; and
        wherein the ion gauge is connected with the low-pressure pipeline through a fourth pneumatic valve,
        wherein pressures of the low-pressure environment simulation unit and the low-pressure pipeline are to be kept at 0.1 Pa to 0.00001 Pa, and temperatures of the low-temperature lunar soil cold trap and the low-temperature water ice cold trap are to be 80 k to 350 k;

the method comprising the following steps:

S1: a preparation of the water-containing simulated lunar soil, the preparation comprising:

opening the first switch valve, the second switch valve, the first pneumatic valve, and the second pneumatic valve, starting the vacuum pump to vacuum, closing the first pneumatic valve and the second pneumatic valve after pressures in the low-pressure pipeline and the preparation pipeline are reduced to preset values, regulating temperatures of the low-temperature lunar soil cold trap and the low-temperature water ice cold trap to enable the solid ice in the low-temperature water ice cold trap to melt and release water vapor to prepare the water-containing simulated lunar soil, and closing the second switch valve after the water-containing simulated lunar soil is prepared successfully; and S2: a measurement of the water content of the water-containing simulated lunar soil, the measurement comprising:

opening the first pneumatic valve and the second pneumatic valve, heating the low-temperature lunar soil cold trap, and measuring the water content by the water content analysis unit.

8. The water-containing simulated lunar soil preparation and water content measurement method according to claim 7, wherein in S1, opening the fourth pneumatic valve to measure the pressures in the low-pressure pipeline and the preparation pipeline after the vacuum pump is started, and closing the first pneumatic valve and the second pneumatic valve after the pressures in the low-pressure pipeline and the preparation pipeline are reduced to 0.00001 Pa.

9. The water-containing simulated lunar soil preparation and water content measurement method according to claim 8, wherein both the first switch valve and the second switch valve are manual angle valves.

10. The water-containing simulated lunar soil preparation and water content measurement method according to claim 8, wherein the vacuum pump is a molecular pump.

11. The water-containing simulated lunar soil preparation and water content measurement method according to claim 7, wherein both the first switch valve and the second switch valve are manual angle valves.

12. The water-containing simulated lunar soil preparation and water content measurement method according to claim 7, wherein the vacuum pump is a molecular pump.

* * * * *